ically in single or divided doses. The dosage varies with the subject, route of administration, symptom and so on. For the injectable preparation, for instance, a dose of about 0.2 to 20 mg/kg body weight is administered 1 to 3 times a day, while for oral administration a dose of about 1 to 100 mg/kg body weight is administered 1 to 3 times a day.

United States Patent [19]
Imada et al.

[11] 4,436,753
[45] Mar. 13, 1984

[54] METHOD FOR THERAPY OF ISCHEMIC DISEASE

[75] Inventors: Isuke Imada, Izumi; Akinobu Nagaoka, Kawanishi; Minoru Hirata, Ikeda, all of Japan

[73] Assignee: Takeda Chemical Industries, Ltd., Osaka, Japan

[21] Appl. No.: 217,538

[22] Filed: Dec. 17, 1980

[30] Foreign Application Priority Data

Dec. 30, 1979 [JP] Japan .................................. 54-171125

[51] Int. Cl.³ .............................................. A61K 31/12
[52] U.S. Cl. .................................................... 424/331
[58] Field of Search ................................... 424/331, 94

[56] References Cited
U.S. PATENT DOCUMENTS
4,139,545 2/1979 Morimoto et al. ............. 260/396 R Primary Examiner—Sam Rosen
Attorney, Agent, or Firm—Wenderoth, Lind & Ponack

[57] ABSTRACT

A mammal suffering from ischemic disease such as cerebral apoplexy, cardiac insufficiency, renal insufficiency due to vascular changes, etc. is remedied by administering to said mammal an effective amount of a compound of the formula:

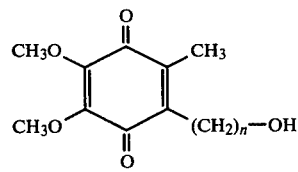

wherein n is an integer of from 4 to 22.

8 Claims, No Drawings

METHOD FOR THERAPY OF ISCHEMIC DISEASE

This invention relates to a method for therapy of ischemic disease.

Cerebral apoplexy and heart diseases now rank high among the causes of death, and therapeutic agents therefor are being searched for extensively.

There are observable cases where ischemic changes in the brain and heart are closely related to the genesis of these diseases, and one of the typical metabolic changes in organ tissues found at the time of such ischemia is depression of energy metabolism. Therefore, the medicines capable of improving the depressed energy metabolism in the tissues, cellular metabolism-improving agents, are used in the treatment of the diseases mentioned above.

However, it is difficult at the present time to find cellular metabolism-improving agents free from adverse effects. For instance, cytochrome C and adenosine triphosphate are known as cellular metabolism-improving agents, but cytochrome C itself sometimes causes shock symptoms in patients having an allergic constitution, while adenosine triphosphate itself sometimes causes adverse reactions such as arrhythmia.

The present inventors have searched extensively for cellular metabolism-improving agents effective in the treatment of such ischemic diseases as cerebral circulatory disturbance, cardiac insufficiency, etc. without producing such side effects, and now have completed the present invention.

This invention relates to:

1. A method for treatment of a mammal suffering from an ischemic disease, which comprises administering to said mammal an effective amount of a compound of the formula:

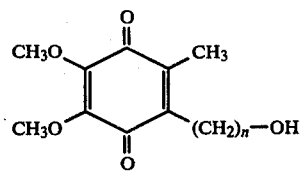
(I)

wherein n is an integer of from 4 to 22, preferably from 6 to 18.

2. A medicinal composition for the treatment of a mammal suffering from an ischemic disease, which comprises, as an active ingredient, an effective amount of a compound of the formula [I] and a physiologically acceptable carrier, excipient or diluent therefor.

3. The use for a therapeutic agent of the compound [I] or the composition as defined above.

The above-mentioned compound [I] may be exemplified by 2,3-dimethoxy-5-methyl-6-(6-hydroxyhexyl)-1,4-benzoquinone, 2,3-dimethoxy-5-methyl-6-(9-hydroxynonyl)-1,4-benzoquinone, 2,3-dimethoxy-5-methyl-6-(10-hydroxydecyl)-1,4-benzoquinone, 2,3-dimethoxy-5-methyl-6-(11-hydroxyundecyl)-1,4-benzoquinone, 2,3-dimethoxy-5-methyl-6-(12-hydroxydodecyl)-1,4-benzoquinone, 2,3-dimethoxy-5-methyl-6-(13-hydroxytridecyl)-1,4-benzoquinone, 2,3-dimethoxy-5-methyl-6-(18-hydroxyoctadecyl)-1,4-benzoquinone, 2,3-dimethoxy-5-methyl-6-(20-hydroxyeicosyl)-1,4-benzoquinone, 2,3-dimethoxy-5-methyl-6-(22-hydroxydocosyl)-1,4-benzoquinone.

The compound [I] can be prepared by a per se known method, for example, the method described in U.S. Pat. No. 4,139,545 or an analogous method thereto, namely, by reacting a compound of the formula:

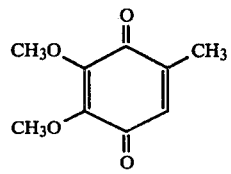
(II)

with a compound of the formula:

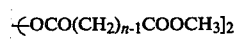
[III]

wherein n has the meaning given above, to give a compound of the formula:

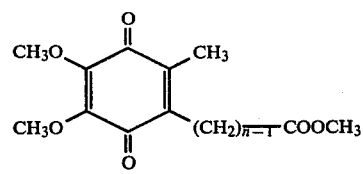
(IV)

wherein n has the meaning given above, and then reducing the compound [IV] by means of a reducing agent, for example, lithium aluminum hydride following oxidation with ferric chloride. The reaction of compound [II] with compound [III] is advantageously conducted in a suitable inert solvent such as, n-hexane, ligorine, toluene, xylene, acetic acid or propionic acid. The reaction temperature is advantageously in the range of about 80° C. to 100° C., and the reaction time is desirably in the range of about 0.5 to 3 hours. For reducing the compound [IV], any procedure may be taken so long as the carboxyl may thereby be converted to an alcoholic hydroxyl. As such procedures, there may be mentioned reduction by means of lithium aluminum hydride. Generally this reduction is advantageously conducted in the presence of such a suitable solvent as diethyl ether, tetrahydrofuran and dioxide.

The compound [I] shows an excellent cellular metabolism-improving activity in mammals (e.g. human being, mouse, rat, rabbit, dog and monkey), and it is used for alleviation or therapy of ischemic diseases especially in the brain, heart and kidneys. Ischemia is a localized tissue anemia due to obstruction of the inflow of arterial blood as by the narrowing of arteries by spasm or disease. The ischemic disease includes cerebral apoplexy (e.g. cerebral infarction, cerebral hemorrhage, cerebral hemorrhagic infarction, cerebral embolus, etc.), cardiac insufficiency (cardiac infarction, angina pectoris, cardiac failure, congestive heart failure, coronary insufficiency, etc.) and renal insufficiency due to vascular changes (nephrosclerosis, proteinuria due to vascular lesions, renovascular hypertension, etc.).

The compound [I] may be safely administered, orally or parenterally, as it is or advantageously as a pharmaceutical composition comprising an effective amount of the compound [I] and a physiologically acceptable carrier, excipient or diluent therefor, in the form of, for example, powder, granule, tablet, hard capsule, soft capsule, dry syrup, suppository, injection or the like.

The composition for oral administration such as powder, granule, tablet, hard capsule, soft capsule and dry syrup may be prepared by a per se known conventional manner, and may comprise carriers, excipients or diluents conventionally used in the pharmaceutical art. For example, suitable carries or excipients include lactose, starch, sugar, magnesium stearate, etc. As the excipients in the preparation of soft capsules, there may be used nontoxic, pharmaceutically acceptable oils and fats of animal, vegetable or mineral origin. The essential active ingredients are generally dissolved in these oils and fats before filling soft capsules therewith.

The compositions for parenteral administration may, for example, be injections and suppositories. The injectable preparations may be prepared in the form of solutions or suspensions. Since compounds [I] are soluble in oil but only sparingly soluble in water, injectable preparations in the form of aqueous solutions may be prepared by using solubilizing agents, if desired. As such solubilizing agents, there may be used nonionic surfactants that have adequate HLB values and are selected from among the nonionic surfactants generally used in the preparation of injectable solutions. The suppositories for rectal administration can be prepared by incorporating the compound [I] with a conventional suppository base.

The composition of this invention contains a drug of dosage unit form. The drug of dosage unit form means a drug containing a daily dose of the compound [I] to be described hereinafter, or its multiples (up to 4 times), or its measures (down to 1/40), which is in the physically separate unit form suitable for administering as a medicine. Each dosage unit generally contains 0.3 mg to 100 mg of the compound [I]. Among them, an injection ampoule preferably contains 0.3 mg to 30 mg, and each of the other forms preferably contains 5 mg to 100 mg of the compound [I].

The dosage of the compound [I] varies with the kinds of diseases, symptoms, administration routes or dosage forms, but, in case of parenteral administration such as injection, for example, intravenous administration, the daily dose as the compound [I] is about 0.3 to 100 mg (0.006 mg to 2 mg/kg), preferably 1 mg to 30 mg (0.02 mg to 0.6 mg/kg) for adult humans, and in case of oral administration, the daily dose is about 5 mg to 600 mg (0.1 mg to 12 mg/kg), preferably 10 mg to 300 mg (0.2 mg to 6 mg/kg) for adult humans.

In a test in rats (each group consisting of 10 rats), when the compounds of the invention were administered at a dose of 500 mg/kg once a day consecutively for 5 weeks, no abnormalities as compared with the control group were observed in any respect, namely in general condition, body weight, food consumption, urinalysis, general hematology, blood biochemistry, examination of liver for lipids, autopsy examination of organs, histopathology, enzymohistology, etc. These doses in rats are 10–5,000 times as much as the clinical doses mentioned above, and therefore it may be said that the compounds practically have no adverse effects from the clinical viewpoint. In this respect, the compounds of the present invention are superior to the cellular metabolism-improving agents so far known.

In the examples described later, the useful pharmacological activity of the compounds of the present invention has been confirmed in rats suffering from spontaneous hypertension. It is known that the strain of rats is very close to humans in such a morbid condition as cerebral apoplexy or cardiac insufficiency, that the drugs effective in humans are also effective in these rats, and that the strain therefore serves as a trustworthy model for the case of application of a drug to humans.

REFERENCE EXAMPLE 1

Methyl 13-chloroformyltridecanoate (11.7 g) is dissolved in 200 ml of petroleum ether. To the solution is added 60 ml of ice water with ice cooling under stirring, and then 5.2 g of sodium peroxide is added to the mixture portionwise. After stirring for an hour, the reaction mixture is extracted with ether. The extract is washed with water and dried over calcium chloride, and the solvent is then distilled off under reduced pressure to give 7.6 g of crude crystals of bis-13-methoxycarboxyltridecanoyl peroxide. This product is submitted to the following step without purification.

IR$\nu_{max}^{film}$ cm$^{-1}$: 1790,

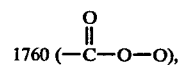

1730 (COOCH$_3$). 2,3-Dimethoxy-5-methyl-1,4-benzoquinone (1.7 g) is dissolved in 20 ml of acetic acid, and 7.6 g of the above bis-13-methoxycarbonyltridecanoyl peroxide is added portionwise thereto with stirring at 90° C. The mixture is heated for 22 hours, cooled, diluted with water and extracted with ether. The extract is washed in sequence with a saturated aqueous sodium chloride solution, an aqueous sodium bicarbonate solution and an aqueous sodium chloride solution, and dried. The solvent is distilled off under reduced pressure and the residue is recrystallized from hexane to give 1.37 g of 2,3-dimethoxy-6-(12-methoxycarbonyldodecyl)-5-methyl-1,4-benzoquinone as orange needles. m.p. 54° C., Elemental analysis: Calculated for $C_{23}H_{36}O_6$: C, 67.62; H, 8.88; Found: C, 67.52; H, 8.59.

Lithium aluminum hydride (740 mg) is suspended in 80 ml of dried ether, and a solution of 1.06 g of 2,3-dimethoxy-6-(12-methoxycarbonyldodecyl)-5-methyl-1,4-benzoquinone in 100 ml of dried ether is added dropwise with stirring and ice cooling. After 1.5 hours, ice water is added so as to decompose the excess lithium aluminum hydride, then acidified with hydrochloric acid and extracted with ether. The extract is washed with water and concentrated under reduced pressure. The residue is dissolved in 30 ml of methanol, a solution of 12 g of ferric chloride in 60 ml of water is added, and the mixture is stirred at room temperature for 1.5 hours. The liquid reaction mixture is diluted with water and extracted with ethyl acetate. The extract is washed with water and dried, and the solvent is distilled off under reduced pressure. The residue is dissolved in chloroform and subjected to silica gel column chromatography. The crystals recovered from the chloroform-ethanol (99:1) eluate are recrystallized from ether-hexane to give 727 mg of 6-(13-hydroxytridecyl)-2,3-dimethoxy-5-methyl-1,4-benzoquinone (in formula I, n=13) as yellow needles. m.p. 65°–66° C.

REFERENCE EXAMPLE 2

One gram of 1,20-eicosanedicarboxylic acid monomethyl ester is dissolved in 5 ml of thionyl chloride. After stirring at room temperature for 12 hours, excess thionyl chloride is distilled off under reduced pressure to give crude crystals of methyl 21-chloroformylheneicosanoate. This product is submitted to the following step without purification.

IR$\nu_{max}^{KBr}$ cm$^{-1}$: 1790, (COCl), 1730 (COOCH$_3$).

Aluminum chloride (2.5 g) is added portionwise in a nitrogen atmosphere to a solution of 1 g of methyl 21-chloroformylheneicosanoate and 1.7 g of 3,4,5-trimethoxytoluene in 50 ml of nitrobenzene, and the resulting mixture is stirred at room temperature for 48 hours. To the reaction mixture are added water and diluted hydrochloric acid, and the whole mixture is extracted with ether. After distilling of the solvent, the residue is dissolved in methanol, 4.6 ml of a 30% sodium hydroxide solution is added, and the mixture is stirred at 60° C. for an hour. The reaction mixture is washed with ether, then made acidic with diluted hydrochloric acid and extracted with ethyl acetate. The extract is washed with water and dried, the solvent distilled off, and the residue chromatographed on silica gel. The crystals recovered from the chloroform-ethanol (17:1) eluate are recrystallized from ether-hexane to give colorless crystals of 21-(2-hydroxy-3,4-dimethoxy-6-methylbenzoyl)-heneicosanoic acid. m.p. 103°–150° C.

To a solution of 3 g of the above 21-(2-hydroxy-3,4-dimethoxy-6-methylbenzoyl)heneicosanoic acid in 10 ml of methanol is added p-toluenesulfonic acid (30 mg), followed by heating under reflux for 2 hours. After cooling to room temperature, water is added and the mixture is stirred at 0° C. to give colorless crystals of methyl 21-(2-hydroxy-3,4-dimethoxy-6-methylbenzoyl)heneicosanoate. m.p. 72°–72.5° C.

To a solution (15 ml) of 3 g of methyl 21-(2-hydroxy-3,4-dimethoxy-6-methylbenzoyl)heneicosanoate in ethyl acetate are added 0.015 ml of 60% perchloric acid and 600 mg of 5% palladium-on-carbon, and catalytic reduction is carried out at a 70° C. using hydrogen gas at the pressure of 100 kg/cm$^2$. The catalyst is filtered off and the filtrate is washed in sequence with ice water, a saturated aqueous sodium bicarbonate solution and a saturated aqueous sodium chloride solution, and dried over anhydrous sodium sulfate. Removal of the solvent by distillation under reduced pressure gives colorless crystals of methyl 22-(2-hydroxy-3,4-dimethoxy-6-methylphenyl)docosanoate. m.p. 71°–72.5° C.

To 30 ml of a solution of 3 g of methyl 22-(2-hydroxy-3,4-dimethoxy-6-methylphenyl)docosanoate in tetrahydrofuran is added lithium aluminum hydride, and the mixture is stirred at room temperature for 1 hour. To the reaction mixture is added 10% sulfuric acid under ice cooling, and the whole mixture is extracted with ether. The extract is washed with water and dried, and then the solvent is distilled off under reduced pressure to give colorless crystals of 6-(22-hydroxydocosyl)-2,3-dimethoxy-5-methylphenol.

Elemental analysis: Calculated for C$_{31}$H$_{54}$O$_4$: C, 75.87; H, 11.09; Found: C, 75.79; H, 11.38.

In dimethylformamide (200 ml) are suspended 6-(22-hydroxydocosyl)-2,3-dimethoxy-5-methyl phenol (300 mg) and bis(4-hydroxysalicylidene)ethylenediiminocobalt(II) (50 mg). The suspension is stirred in an oxygen gas stream at ambient temperature and atmospheric pressure for 7 days. The insoluble matter is filtered off and the filtrate is concentrated under reduced pressure. The residue is diluted with water and extracted with ethyl acetate. The extract is treated in a conventional manner and the product is chromatographed on a silica gel column. The fractions obtained by elution with chloroform are pooled and recrystallized from ethanol to give orange-yellow needles of 6-(22-hydroxydocosyl)-2,3-dimethoxy-5-methyl-1,4-benzoquinone (I, n=22). m.p. 89°–90.5° C.

REFERENCE EXAMPLE 3

To a solution (150 ml) of 11-acetoxy-n-undecanoyl chloride (27.6 g) in 1,2-dichloroethane is added aluminum chloride (28 g), and the mixture is stirred at room temperature for 2 hours. The reaction mixture is cooled to 5° C. followed by addition of a solution (50 ml) of 3,4,5-trimethoxytoluene (19.1 g) in 1,2-dichloroethane and the whole mixture is stirred at room temperature for 72 hours. The reaction mixture is then heated to 50°–60° C. and stirred for 30 minutes. After cooling, 300 ml of ice water is added to the reaction mixture and the product is extracted with dichloromethane. The dichloromethane layer is washed with water and dried over anhydrous magnesium sulfate, and the solvent is distilled off to give a light-yellow oil of 6-(11-acetoxy-1-oxoundecyl)-2,3-dimethoxy-5-methylphenol (33 g).

IR$\nu_{max}^{Neat}$ cm$^{-1}$: 1730 (OAc), 1680 (CO), 1610, 1580 (Ar).

Ms m/e: 394(M+), 352, 334, 195.

To a solution (300 ml) of 6-(11-acetoxy-1-oxoundecyl)-2,3-dimethoxy-5-methylphenol (34 g) in methanol is added sodium hydroxide (7 g), and the mixture is stirred at room temperature for 2 hours. After 5 N hydrochloric acid is added to the reaction mixture to neutralize, the solvent is distilled off to give crude crystals. The product is washed with water and recrystallized from ether-hexane (1:1) to give colorless needles of 6-(11-hydroxy-1-oxoundecyl)-2,3-dimethoxy-5-methylphenol (30 g). m.p. 81° C.

To a solution (200 ml) of 6-(11-hydroxy-1-oxoundecyl)-2,3-dimethoxy-5-methylphenol (14 g) in acetic acid is added 5% palladium-on-carbon (50% hydrate; 3 g) and 70% perchloric acid (0.1 ml), and catalytic reduction is carried out at ambient temperature and atmospheric pressure. After completion of the absorption of hydrogen, the catalyst is filtered off and the filtrate is concentrated under reduced pressure. The residue is extracted with dichloromethane, and the dichloromethane layer is washed with 5% aqueous sodium bicarbonate and dried over anhydrous sodium sulfate. Removal of the solvent by distillation gives a colorless oil of 6-(11-acetoxyundecyl)-2,3-dimethoxy-5-methylphenol (15 g).

IR$\nu_{max}^{Neat}$ cm$^{-1}$: 3450 (OH), 1730 (OAc), 1610, 1580 (Ar).

To a solution (400 ml) of 6-(11-acetoxyundecyl)-2,3-dimethoxy-5-methylphenol (8 g) in dimethylformamide are added potassium nitrosodisulfonate (24 g), water (400 ml), methanol (30 ml) and potassium dihydrogen phosphate (1.0 g), and the mixture is stirred at room temperature for 28 days. The product is extracted with dichloromethane and the dichloromethane layer is washed with water and then dried over anhydrous magnesium sulfate. Removal of the solvent by distillation gives crude crystals. Recrystallization from hexane yields orange-yellow needles of 6.4 g of 6-(11-acetoxyundecyl)-2,3-dimethoxy-5-methyl-1,4-benzoquinone. m.p. 41° C.

To a solution (200 ml) of 6-(11-acetoxyundecyl)-2,3-dimethoxy-5-methyl-1,4-benzoquinone (4.2 g) in methanol is added concentrated hydrochloric acid (0.1 ml), and the mixture is allowed to stand at room temperature for 12 hours. To the reaction mixture is added sodium bicarbonate (0.2 g) and the solvent is distilled off. The product is dissolved in dichloromethane and the insoluble matter is filtered off. Removal of dichloromethane by distillation gives crude crystals. Recrystallization from hexane-ether (3:1) yields orange-yellow needles of 6-(11-hydroxyundecyl)-2,3-dimethoxy-5-methyl-1,4-benzoquinone (I, n=11) (3.6 g) m.p. 57° C.

REFERENCE Example 4

To a solution (30 ml), of 12-acetoxy-n-dodecanoyl chloride (8.5 g) in 1,2-dichloroethane is added aluminum chloride (8.2 g), and the mixture is stirred at room temperature for 2 hours. The reaction mixture is cooled to 5° C., followed by addition of a solution (20 ml) of 3,4,5-trimethoxytoluene (5.6 g) in 1,2-dichloroethane and the mixture is stirred at room temperature for 72 hours. The whole mixture is heated to 50°–60° C. and stirred for 30 minutes. Further, to this reaction mixture is added methanol (200 ml) and the resulting mixture is stirred at 50° C. for 3 hours. The solvent is distilled off and the residue is extracted with dichloromethane. The dichloromethane layer is washed with water, dried over anhydrous magnesium sulfate, and the solvent is distilled off to give crude crystals. The product is recrystallized from ether-hexane (1:1) to give colorless needles of 6-(12-hydroxy-1-oxodecyl)-2,3-dimethoxy-5-methylphenol (8.5 g). m.p. 82° C.

To a solution (150 ml) of 5-(12-hydroxy-1-oxododecyl)-2,3-dimethoxy-5-methylphenol (6.4 g) in acetic acid are added 5% palladium-on-carbon (50% hydrate; 1.1 g) and 70% perchloric acid (0.1 ml), and catalytic reduction is carried out at ambient temperature and atmospheric pressure. After completion of the adsorption of hydrogen, the catalyst is filtered off and the filtrate is concentrated under reduced pressure. The residue is extracted with dichloromethane. The dichloromethane layer is washed with a 5% aqueous sodium bicarbonate solution and dried over anhydrous magnesium sulfate. The solvent is distilled off to give a colorless oil of 6-(12-acetoxydodecyl)-2,3-dimethoxy-5-methylphenol (6.8 g).

IR$\nu_{max}^{Neat}$ cm$^{-1}$: 3450 (OH), 1730 (OAc), 1610, 1580 (Ar).

To a solution (300 ml) of 6-(12-acetoxydodecyl)-2,3-dimethoxy-5-methylphenol (6.1 g) in dimethylformamide are added potassium nitrosodisulfonate (18 g), water (300 ml), methanol (50 ml) and potassium dihydrogen phosphate (0.5 g), and the mixture is stirred at room temperature for 30 days. The product is extracted with dichloromethane, and the organic layer is washed with water and dried over anhydrous magnesium sulfate. The solvent is distilled off to give crude crystals. This product is recrystallized from hexane to give orange-yellow needles of 6-(12-acetoxydodecyl)-2,3-dimethoxy-5-methyl-1,4-benzoquinone (4.8 g). m.p. 47° C.

To a solution (200 ml) of 6-(12-acetoxydodecyl)-2,3-dimethoxy-5-methyl-1,4-benzoquinone (4.4 g) in methanol is added concentrated hydrochloric acid (0.1 ml) and the mixture is allowed to stand at room temperature for 12 hours. To this reaction mixture is added sodium bicarbonate (0.2 g), and the solvent is distilled off. The product is dissolved in dichloromethane, the insoluble matter is filtered off and the dichloromethane is distilled off to give crude crystals. Recrystallization from hexane-ether (3:1) gives orange-yellow needles of 6-(12-hydroxydodecyl)-2,3-dimethoxy-5-methyl-1,4-benzoquinone (3.8 g). m.p. 63° C.

REFERENCE EXAMPLE 5

To a solution (50 ml) of 18-acetoxy-n-octadecanoyl chloride (11 g) in 1,2-dichloroethane is added aluminum chloride (7 g), and the mixture is stirred at room temperature for 2 hours. The reaction mixture is cooled to 5° C., followed by addition of a solution (20 ml) of 3,4,5-trimethoxytoluene (6.2 g) in 1,2-dichloroethane. The whole mixture is stirred at room temperature for 72 hours. Further, the reaction mixture is heated to 50°–60° C. and stirred for 30 minutes. After cooling, ice water is added and the product is extracted with dichloromethane. The dichloromethane layer is washed with water and the solvent is distilled off to give an oil (12.1 g). The oil is dissolved in methanol (150 ml) followed by addition of sodium hydroxide (5.2 g) and stirring at room temperature for 2 hours. The reaction mixture is neutralized with 5 N hydrochloric acid and the solvent is distilled off to give crude crystals. Washing the product with water and recrystallization from dichloromethane-ether (1:1) give colorless needles of 6-(18-hydroxy-1-oxooctadecyl)-2,3-dimethoxy-5-methylphenol (6.4 g). m.p. 101° C.

To a solution (30 ml) of 6-(18-hydroxy-1-oxooctadecyl)-2,3-dimethoxy-5-methylphenol (1.4 g) in acetic acid are added 5% palladium-on-carbon (50% hydrate; 0.5 g) and 70% perchloric acid (0.05 ml), and catalytic reduction is carried out at ambient temperature under atmospheric pressure. After completion of the absorption of hydrogen, the catalyst is filtered off and the filtrate is concentrated under reduced pressure to give a colorless oil. The oil is dissolved in ether, the ether layer is washed with a 5% aqueous sodium bicarbonate solution and dried over anhydrous sodium sulfate, and the solvent is distilled off to give crude crystals. Recrystallization from hexane gives colorless needles of 6-(18-acetoxyoctadecyl)-2,3-dimethoxy-5-methylphenol (1.4 g). m.p. 53° C.

6-(18-Hydroxyoctadecyl)-2,3-dimethoxy-5-methylphenol (0.5 g), prepared by deacetylating the above 18-acetoxy compound in the same manner as in Reference Example 3, is dissolved in dimethylformamide (1 l) followed by addition of potassium nitrosodisulfonate (13 g), water (700 ml), methanol (100 ml) and potassium-dihydrogen phosfate (1 g). The mixture is stirred at room temperature for 45 days. The product is extracted in a conventional manner and recrystallized from hexane to give yellow needles of 6-(18-hydroxyoctadecyl)-2,3-dimethoxy-5-methyl-1,4-benzoquinone (I, n=18, 0.31 g). m.p. 81° C.

REFERENCE EXAMPLE 6

To a solution (20 ml) of 6-(12-acetoxydodecyl)-2,3-dimethoxy-5-methylphenol (1.1 g) in dimethylformamide is added bis(salicylidene)ethylenediiminocobalt(II) (40 mg), and the mixture is stirred at room temperature in an oxygen gas stream at atmospheric pressure for 72 hours. The solvent is distilled off and the product is extracted with ether. The ether layer is washed with water and dried over anhydrous sodium sulfate, and solvent is distilled off to give crude crystals. Recrystallization from ether-hexane (1:1) gives orange-yellow needles of 6-(12-acetoxydodecyl)-2,3-dimethoxy-5-methyl-1,4-benzoquinone (0.84 g). m.p. 47° C.

The product is treated with concentrated hydrochloric acid in methanol as in the corresponding step in Reference Example 4, whereby the compound of formula I wherein n=12 is obtained.

REFERENCE EXAMPLE 7

To a solution (80 ml) of 6-(20-hydroxyeicosyl)-2,3-dimethoxy-5-methylphenol (0.6 g) in tetrahydrofuran is added an aqueous solution (20 ml) of potassium persulfate (2.7 g), and the mixture is stirred at room temperature in a nitrogen gas stream for 72 hours. The product is extracted rapidly with ether and the ether is distilled off. To the residue, 6-(20-hydroxyeicosyl)-2,3-dimethoxy-5-methylhydroquinone, is added 1 ml of acetic anhydride and the resulting mixture is allowed to stand at room temperature for 3 hours. The product is extracted in a conventional manner and recrystallized from hexane to give colorless needles of 6-(20-acetoxyeicosyl)-2,3-dimethoxy-5-methylhydroquinone-1,4-diacetate (0.31 g). m.p. 67° C.

In accordance with the corresponding steps in Reference Example 3, this product is treated with concentrated methanolic hydrochloric acid and then with methanolic ferric chloride to give the compound of formula I where n=20.

REFERENCE 8

The compound of the present invention (I, n=10) was suspended in a gum arabic solution and oraly administered consecutively for 2 weeks at a daily dose of 100 mg/kg or 500 mg/kg, and examination of general condition, urinalysis and blood examination were carried out during the course of administration. Histopathology was done at the termination of the administration. The results could not reveal any abnormalities ascribable to the administration.

EXAMPLE 1

Mitochondrial Respiration Activating Effect

The effect of activating the respiration of bovine heart mitochondria deactivated by treatment with acetone was evaluated by the method of Lester and Fleischer (Biochim. Biophys. Acta, vol. 113, p. 519, 1966). The respiration activating effect was expressed in terms of oxygen consumption due to succinate oxidase activity, succinic acid being the substrate. The results, as shown in Table 1, revealed that an increase in oxygen consumption was caused in the groups in which the compounds of the invention were added, showing the respiration activating effect thereof.

TABLE 1

Effect of activating the respiration of deactivated mitochondria

| Compound added | Amount added (n mole) | Oxygen consumption rate* Oxygen (n atom)/minute/ mg protein | n** |
|---|---|---|---|
| No addition (control) | 0 | 7.1 ± 2.8 | 4 |
| I (n = 10) | 5 | 45.0 ± 3.7 | 5 |
| I (n = 18) | 5 | 44.5 ± 3.2 | 3 |

*The rate was measured at 23° C. using an oxygen electrode apparatus (Gilson's model K-IC). Composition of the reaction medium (2 ml): 0.2 M sucrose, 10 mM Tris-hydrochloric acid (pH 7.4), 20 mM KCl, 3 mM $MgCl_2$, 50 μM EDTA.2Na, 1.99 mg (as protein) acetone-treated mitochondria, 50 μM potassium succinate, 0.2 mg cytochrome C, and 5 μl 1% Nikkol OP-10 ® (polyoxyethylene octylphenyl ether; Produced by Nikko Chemicals) solution of the test sample (in the case of the test sample) or 5 μl 1% Nikkol OP-10 ® (Polyoxyethylene octylphenyl ether; Produced by Nikko Chemicals) (in the case of the control).
**Number of Experiments

EXAMPLE 2

Cerebral Ischemia-Protecting Effect

Spontaneously hypertensive rats showing a strong tendency to cerebral apoplexy (hereinafter abbreviated to SHRSP) (Okamoto et al., Circulation Res., vol. 34–35, pp. 1–143, 1974), were newly established in 1974. When the carotid artery is ligated on both sides, apoplectic symptoms such as convulsion fit, respiratory distress and coma, which lead to death (the incidence being 100%), are observed.

Oral administration of the compound of the invention (15 mg/kg) consecutively for 3 weeks significantly retarded the manifestation of the apoplectic symptoms, as seen in Table 2. The time to the manifestation of the symptoms and the time to death were prolonged also by the administration of 100 mg/kg for 3 days or 35 mg/kg for 14 days.

TABLE 2

Cerebral ischemia protecting effect

| Experiment No. | Compound | Dose (mg/kg/day) | Administration period (days) | Number of rats | Time to convulsion fit (minutes) | Time to death (minutes) |
|---|---|---|---|---|---|---|
| 1 | Control | — | — | 10 | 85 ± 9 | — |
|   | I(n = 10) | 15 | 21 | 10 | 119 ± 13* | — |
| 2 | Control | — | — | 8 | 79 ± 8 | 148 ± 21 |
|   | I(n = 10) | 100 | 3 | 8 | 117 ± 15* | 235 ± 27* |
| 3 | Control | — | — | 8 | 62 ± 9 | 156 ± 20 |
|   | I(n = 10) | 35 | 14 | 8 | 93 ± 14 | 242 ± 29* |

*P <0.05 (Student's t-test)

EXAMPLE 3

Cerebral Apoplexy Preventing Effect

The SHRSP, fed with high sodium chloride level, are liable to develop cerebral apoplexy (cerebral hemorrhage or hemorrhagic infarction) with high incidence. The compound of the invention (I, n=10) was administered in admixture with the diet to a group of 12 male SHRSP. When compared with the control group (no administration), cerebral apoplexy was significantly (P<0.05 by Wilcoxon's two sample test) inhibited in the group given the compound of the invention.

On the other hand, the effect of the compound of the invention upon the spontaneous manifestation of cerebral apoplexy was examined in a group of 10 SHRSP fed without sodium chloride loading, and it was found that the compound can prevent manifestation of cerebral apoplexy as in the above case.

TABLE 3

| Cerebral apoplexy preventing effect | | | | |
|---|---|---|---|---|
| Experiment No. | Sodium chloride loading | Compound (mg/kg/day) | Administration period (days) | Incidence of cerebral apoplexy[3] |
| 1[1] | + | 0 | — | 12/12 |
|  |  | 35 | 40 | 7/12 |
| 2[2] | — | 0 | — | 10/10 |
|  |  | 35 | 45 | 5/10 |

[1] 8-week-old male SHRSP
[2] 14-week-old male SHRSP
[3] Number of apoplectic cases/number of animals used.

EXAMPLE 4

Improving Effect on Symptoms of Cerebral Apoplexy

SHRSP's were fed under sodium chloride loading as in Example 3. Upon manifestation of the first symptom, the sodium chloride loading was discontinued and at the same time oral administration of the compound of the invention (I, n=10) was commenced. After administration for 3 weeks, the dosed group was compared with the control group in respect of the severity of the symptoms. The severity was scored (0 for no symptoms to 5 for the severest) for each individual and the results were expressed in terms of the total score for the respective group. As shown by the results set forth in Table 4, the administration of the compound of the present invention alleviated the clinical symptoms after manifestation of the apoplexy. The body weight loss after the apoplexy was also depressed.

TABLE 4

| Improving effect on symptoms of cerebral apoplexy | | | |
|---|---|---|---|
| Compound (mg/kg/day) | Administration period (days) | Severity of symptoms | Body weight loss (%) |
| 0 | — | 35 ± 5 | 15 ± 3 |
| 100 | 21 | 20 ± 3* | 8 ± 3 |

*P <0.05 (Student's t-test)

EXAMPLE 5

Antihypertensive Action

As seen in Table 5, oral administration of the compound of the invention (I, n=10) at a daily dose of 35 mg/kg depressed the blood pressure increase in SHRSP's.

TABLE 5

| Antihypertensive effect | | |
|---|---|---|
| Day of measurement (administration period) | Group[1] | Blood pressure (mmHg) |
| 0 | Control | 176 ± 3 |
|  | Compound of the invention | 175 ± 3 |
| 7 | Control | 193 ± 3 |
|  | Compound of the invention | 188 ± 4 |
| 14 | Control | 213 ± 3 |
|  | Compound of the invention | 199 ± 3* |
| 21 | Control | 225 ± 3 |
|  | Compound of the invention | 208 ± 4* |

[1] Each group consisted of 12 animals.
*P <0.05 (Student's t-test)

The compound of the invention also suppressed a development of malignant hypertension, judging from proteinuria and body weight loss which are indexes of aggravation of hypertension. The kidney of each normal rat was unilaterally excised, and desoxycorticosterone acetate (10 mg/kg) was administered subcutaneously once a week. The rats were given a 1% aqueous sodium chloride solution as drinking water. On the day of operation and thereafter, the compound of the invention (I, n=10) was orally administered at a dose of 50 mg/kg twice a day, and the above indexes of aggravation were determined. As seen in Table 6, the compound of the present invention inhibited the aggravation development of malignant hypertension.

TABLE 6

| Preventing effect against development of malignant hypertension | | | |
|---|---|---|---|
| Day of measurement | Group | Urine protein (mg/day/250 g body weight) | Body weight (g) |
| 0 | Control | 50 ± 2 | 222 ± 4 |
|  | Compound of the invention | 47 ± 1 | 224 ± 4 |
| 14 | Control | 354 ± 38 | 253 ± 10 |
|  | Compound of the invention | 225 ± 38* | 269 ± 8 |
| 21 | Control | 713 ± 83 | 235 ± 12 |
|  | Compound of the invention | 367 ± 68* | 274 ± 13* |

*P <0.05 (Student's t-test)

EXAMPLE 6

Protecting Effect Against Heart Failure

The compounds of the present invention exhibit a protecting effect against heart failure. Adriamycin (1 mg/kg/day) was intraperitoneally administered to normal rats and, after 2 weeks, the compound of the invention (I, n=10) (10 mg/kg/day) was orally administered, and the cardiac functional state was examined electrocardiographically and biochemically. As a result, as seen in Table 7, the widening of the QRS wave interval, an index of heart failure, was prevented. In addition, the tissue lactic acid level, an index of myocardinal energy state, was lowered.

These effects were also demonstrated in the drug-induced cardiac insufficiency in rats suffering from spontaneous hypertension.

TABLE 7

| Protecting effect against heart failure | | | | |
|---|---|---|---|---|
| Rats | Group | Administration period (days) | QRS width (MSEC) | Heart lactic acid ($\mu$moles/g) on wet weight basis |
| Normal rats | Control | — | 7.0 ± 0.5 | 1.8 ± 0.15 |
|  | Compound of the invention | 10 | 4.6 ± 0.4* | 1.65 ± 0.1 |
| Spontaneously | Control | — | 4.8 ± 0.5 | 2.6 ± 0.1 |

TABLE 7-continued

Protecting effect against heart failure

| Rats | Group | Administration period (days) | QRS width (MSEC) | Heart lactic acid ($\mu$moles/g) on wet weight basis |
|---|---|---|---|---|
| hypertensive rats | Compound of the invention | 10 | 2.9 ± 0.2** | 1.9 ± 0.12*** |

*P <0.05
**P <0.01
***P <0.001 (Student's t-test)

EXAMPLE 7

| | |
|---|---|
| Compound of the invention (e.g. I, n = 10) | 30 mg |
| Microcrystalline cellulose | 30 mg |
| Lactose | 57 mg |
| Magnesium stearate | 3 mg |
| Total | 120 mg |

The above ingredients are mixed in a conventional manner and gelatin capsules are filled with the mixture to prepare capsules.

EXAMPLE 8

| | |
|---|---|
| Compound of the invention (e.g. I, n = 10) | 30 mg |
| Lactose | 44 mg |
| Starch | 10.6 mg |
| Starch (for making paste) | 5 mg |
| Magnesium stearate | 0.4 mg |
| Carboxymethylcellulose calcium | 20 mg |
| Total | 110 mg |

The above ingredients are mixed and made into tablets in a conventional manner.

EXAMPLE 9

In 2 g of Nikkol HCO-120 ®(Polyoxyethylene hydrogenated ricinolate; Produced by Nikko Chemicals) is dissolved with warming 0.2 g of the compound of the invention (e.g. I, n=10). To the solution are added 0.4 g of monosodium phosphate and 0.1 g of disodium phosphate to make the pH about 6. There are further added 0.9 g of sodium chloride and 1 g of benzyl alcohol, and then distilled water is added to make the whole volume 100 ml. The mixture is filled in containers, followed by sealing and heat sterilization to prepare an injectable solution.

EXAMPLE 10

| | |
|---|---|
| Compound of the invention (e.g. I, n = 10) | 30 mg |
| Corn oil | 110 mg |
| Total | 140 mg |

The above ingredients are mixed to make a solution and then soft capsules are filled with the solution in a conventional manner.

What is claimed is:

1. A method of improving cellular metabolism in the treatment of ischemic diseases comprising cerebral infarction, cerebral hemorrhage, cerebral hemorrhagic infarction, cerebral embolus, cardiac failure, nephrosclerosis, proteinuria due to vascular lesion and renovascular hypertension, which comprises administering to a mammal suffering from the disease a compound of the formula:

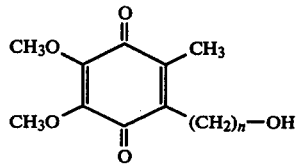

wherein n is an integer of from 4 to 22, in an amount of about 0.006 mg to 12 mg per kilogram of body weight of the mammal per day.

2. A method as claimed in claim 1, wherein the compound is administered orally in an amount of about 0.1 mg to 12 mg per kilogram of body weight of the mammal per day.

3. A method as claimed in claim 1, wherein the compound is administered intravenously in an amount of about 0.006 mg to 2 mg per kilogram of body weight of the mammal per day.

4. A method as claimed in claim 1, wherein n in the formula is an integer of from 6 to 18.

5. A method as claimed in claim 1, wherein the compound is 2,3-dimethoxy-5-methyl-6-(10-hydroxydecyl)-1,4-benzoquinone.

6. A method as claimed in claim 1, wherein the compound is 2,3-dimethoxy-5-methyl-6-(11-hydroxyundecyl)-1,4-benzoquinone.

7. A method as claimed in claim 1, wherein the compound is 2,3-dimethoxy-5-methyl-6-(12-hydroxydodecyl)-1,4-benzoquinone.

8. A method as claimed in claim 1, wherein the compound is 2,3-dimethoxy-5-methyl-6-(13-hydroxytridecyl)-1,4-benzoquinone.

* * * * *